United States Patent [19]

Stone

[11] Patent Number: 5,782,915
[45] Date of Patent: Jul. 21, 1998

[54] ARTICULAR CARTILAGE HETEROGRAFTS

[76] Inventor: Kevin R. Stone, 1 Throckmorton La., Mill Valley, Calif. 94941

[21] Appl. No.: 779,280

[22] Filed: Jan. 6, 1997

Related U.S. Application Data

[63] Continuation of Ser. No. 529,200, Sep. 15, 1995, abandoned.
[51] Int. Cl.$^6$ .................................................. A61F 2/02
[52] U.S. Cl. .............................. 623/11; 623/13; 623/16; 623/20; 623/901; 128/898
[58] Field of Search ............................ 623/11, 13, 17, 623/15, 16, 18, 20, 22, 19, 23, 66, 901; 128/898

[56] References Cited

U.S. PATENT DOCUMENTS

| | | |
|---|---|---|
| 4,034,418 | 7/1977 | Jackson et al. |
| 4,344,193 | 8/1982 | Kenny. |
| 4,502,161 | 3/1985 | Wall. |
| 4,597,266 | 7/1986 | Entrekin. |
| 4,609,627 | 9/1986 | Goldstein. |
| 4,627,853 | 12/1986 | Campbell et al. ............... 623/16 |
| 4,678,470 | 7/1987 | Nashef et al. ................... 623/16 |
| 4,776,853 | 10/1988 | Klement et al. |
| 4,801,299 | 1/1989 | Brendel et al. |
| 4,880,429 | 11/1989 | Stone. |
| 4,932,973 | 6/1990 | Gendler. |
| 5,007,934 | 4/1991 | Stone. |
| 5,067,962 | 11/1991 | Campbell et al. |
| 5,078,744 | 1/1992 | Chvapil ........................... 623/13 |
| 5,092,894 | 3/1992 | Kenny. |
| 5,116,374 | 5/1992 | Stone. |
| 5,158,574 | 10/1992 | Stone. |
| 5,171,273 | 12/1992 | Silver et al. ..................... 623/13 |
| 5,171,322 | 12/1992 | Kenny. |
| 5,192,312 | 3/1993 | Orton ............................... 623/2 |
| 5,306,304 | 4/1994 | Gendler. |
| 5,306,311 | 4/1994 | Stone et al. ..................... 623/18 |
| 5,358,525 | 10/1994 | Fox et al. |
| 5,507,810 | 4/1996 | Prewett et al. |
| 5,613,982 | 3/1997 | Goldstein. |

FOREIGN PATENT DOCUMENTS

| | | |
|---|---|---|
| WO 84/03036 | 8/1984 | WIPO. |
| WO 95/26740 | 10/1995 | WIPO. |
| WO 95/28412 | 10/1995 | WIPO. |
| WO 95/33828 | 12/1995 | WIPO. |

OTHER PUBLICATIONS

Collins et al., (1994) Xenotransplantation, Characterization of Porcine Endothelial Cell Determinants Recognized by Human Natural Antibodies, 1:36–46.

Satake et al., (1994) Xenotransplantation, Limited Specificity of Xenoantibodies In Diabetic Patients Transplanted With Fetal Porcine Islet Cell Clusters, Main Antibody Reactivity Against α–linked Galactose–Containing Epitopes, 1:89–101.

LaVecchio et al., (1995) Transplantation, Enzymatic Removal of Alpha–Galactosyl Epitopes From Porcine Endothelial Cells Diminishes The Cytotoxic Effect of Natural Antibodies, vol. 60, 841–847.

Stone et al. (1993) Arthroscopy: the Journal of Arthroscopic and Related Surgery, 9:234–237.

(List continued on next page.)

*Primary Examiner*—John G. Weiss
*Assistant Examiner*—Francis K. Cuddihy
*Attorney, Agent, or Firm*—Lappin & Kusmer LLP

[57] ABSTRACT

The invention provides an article of manufacture comprising a substantially non-immunogenic articular cartilage heterograft for implantation into humans. The invention further provides a method for preparing an articular cartilage heterograft by removing at least a portion of an articular cartilage from a non-human animal to provide a heterograft; washing the heterograft in saline and alcohol; subjecting the heterograft to at least one treatment selected from the group consisting of exposure to ultraviolet radiation, immersion in alcohol, ozonation, freeze/thaw cycling, and optionally to chemical crosslinking. In accordance with the invention the heterograft has substantially the same mechanical properties as the native xenogeneic articular cartilage.

6 Claims, 1 Drawing Sheet

OTHER PUBLICATIONS

Coterell et al. (1995) Transplantation, The Humoral Immune Response in Humans Following Cross–Perfusion of Porcine Organs, vol. 60, 861–868.

Galili, Immunology Today (1993), vol. 14, No. 10, 480–482.

Elves M.W. et al., An investigation Into The Immunogenicity Of Various Components Of Osteoarticular Grafts, The British Journal of Experimental Pathology, vol. 55, No. 4, pp. 344–351, Aug. 1974.

5,782,915

ARTICULAR CARTILAGE HETEROGRAFTS

This is a continuation of application Ser. No. 08/529,200 filed on Sep. 15, 1995 abandoned.

The present invention relates to the field of treatment of injured human joints, and in particular, to replacement and repair of a damaged human joint articular cartilage using a substantially immunologically compatible articular cartilage from a non-human animal.

BACKGROUND OF THE INVENTION

Articular cartilage covers the ends of all bones that form articulating joints in humans and animals. The cartilage acts in the joint as a mechanism for force distribution and as a lubricant in the area of contact between the bones. Without articular cartilage, stress concentration and friction would occur to the degree that the joint would not permit ease of motion. Loss of the articular cartilage usually leads to painful arthritis and decreased joint motion.

It is known that chondrocytes, the cells that produce articular cartilage, have the ability to migrate into a defect filled with a fibrin clot and form tissue substantially similar to natural cartilage. Additionally, it has been shown that chondrocytes in tissue culture are capable of cell division and matrix synthesis (Webber et al. (1985) *J. Ortho. Res.* 3(1):36). However, the amount of cartilage formed by these procedures is generally not adequate to replace severely damaged joint surfaces in vivo.

Since joint cartilage in adults does not naturally regenerate to a significant degree once it is destroyed, damaged adult articular cartilage has historically been treated by a variety of surgical interventions including repair, replacement, or by excision. With repair or excision, regeneration of tissue may occur, although the tissue is usually temporary and inadequate to withstand the normal joint forces.

Replacement of articular cartilage usually has been by allografting (Sengupta et al. (1974) *J. Bone Surg.* 56B(1) :167–177; Rodrigo et al. (1978) *Clin Orthoo.* 134:342–349) by periosteal grafts (see, e.g., Engkvist (1979) *Scan J. Plast. Reconstr. Surg.* 13:361–369; Rubak (1982) *Acta Orthop. Scan.* 53:181–186) or with metal and/or plastic components (Rubash et al., eds. (1991) *Clin. Orth. Rel. Res.* 271:2–96). Allografting dead cartilage tissue has been tried for years with minimal success. This approach has been only partially successful over the long term due to the host's immunologic response to the graft, failures in the cryopreservation process, and failures of the attachment sites. Replacement of an entire joint surface with metal and plastic components has met excellent success for the older, more sedentary patients, but is generally considered insufficient for tolerating the impact of athletic activities, and has not been shown to restore normal joint mechanics.

In alternative prior art approaches, articular cartilage has been replaced with prostheses composed of bone and/or artificial materials. For example, U.S. Pat. No. 4,627,853 describes the use of demineralized allogenic or xenogenic bone segments as replacements. The proper functioning of these replacements depends on the differential demineralization of the bone segments. U.S. Pat. No. 4,846,835 describes a grafting technique for transplantation of chondrocytes to promote healing lesions in articular cartilage. U.S. Pat. No. 4,642,120 describes the use of gel-like compositions containing embryonal chondrocytes. U.S. Pat. No. 5,306,311 describes a prosthetic articular cartilage which includes a dry, porous volume matrix adapted to have in vivo an outer contour substantially the same as that of natural articular cartilage.

Despite these developments, the replacement of cartilage tissue with structures consisting of permanent artificial materials generally has been less than satisfactory, and a structure suitable as articular cartilage and constructed from natural resorbable materials, or analogs thereof, has not been developed. Because the opposing articular cartilage of mammalian joints is so fragile, it will not withstand abrasive interfaces nor compliance variances from normal which eventually result from the implantation of prior art artificial cartilage. Additionally, joint forces are multiples of body weight which, in the case of the knee and hip, are typically encountered over a million cycles per year. Thus far, prior art permanent artificial cartilages have not been composed of materials having natural articular cartilage properties, nor have they been able to be positioned securely enough to withstand such routine forces.

Much of the structure and many of the properties of original tissues may be retained in transplants through use of xenogeneic or heterograft materials, that is, tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel heterografts are disclosed in WO 84/03036. However, none of these disclosures describe the use of a xenograft for articular cartilage replacement.

Xenograft materials must be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the sidechain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

A need for an improved replacement for articular cartilage which is biocompatible, soft, lubricating, and durable continues to exist.

SUMMARY OF THE INVENTION

The present invention provides a substantially non-immunogenic articular cartilage heterograft for implantation into a human in need of articular cartilage repair. The invention further provides methods for processing xenogeneic articular cartilage with reduced immunogenicity but with substantially native elasticity and load-bearing capabilities for heterografting into humans. The method of the invention, which may include, alone or in combination, treatment with radiation, one or more cycles of freezing and thawing, treatment with a chemical cross-linking agent, treatment with alcohol, or ozonation, provides a heterograft having substantially the same mechanical properties of a native articular cartilage.

In one embodiment, the invention provides an article of manufacture comprising a substantially non-immunogenic articular cartilage heterograft for implantation into a human.

In another embodiment, the invention provides a method of preparing an articular cartilage heterograft for implantation into a human, which comprises removing at least a portion of an articular cartilage from a joint of a non-human animal to provide a heterograft; washing the heterograft in water and alcohol; and subjecting the heterograft to at least one treatment selected from the group consisting of exposure to ultraviolet radiation, immersion in alcohol, ozonation, and freeze/thaw cycling, whereby the heterograft has substantially the same mechanical properties as the articular cartilage.

In another embodiment, the invention provides a method of implanting an articular cartilage heterograft on a surface of an articular joint in a human, comprising the steps of preparing said surface, and affixing a substantially non-immunogenic articular cartilage heterograft to said surface.

BRIEF DESCRIPTION OF THE DRAWINGS

The various features of the invention may be more fully understood from the following description when read together with the accompanying drawing.

DETAILED DESCRIPTION OF THE PREFERRED EMBODIMENTS

Figure 1:
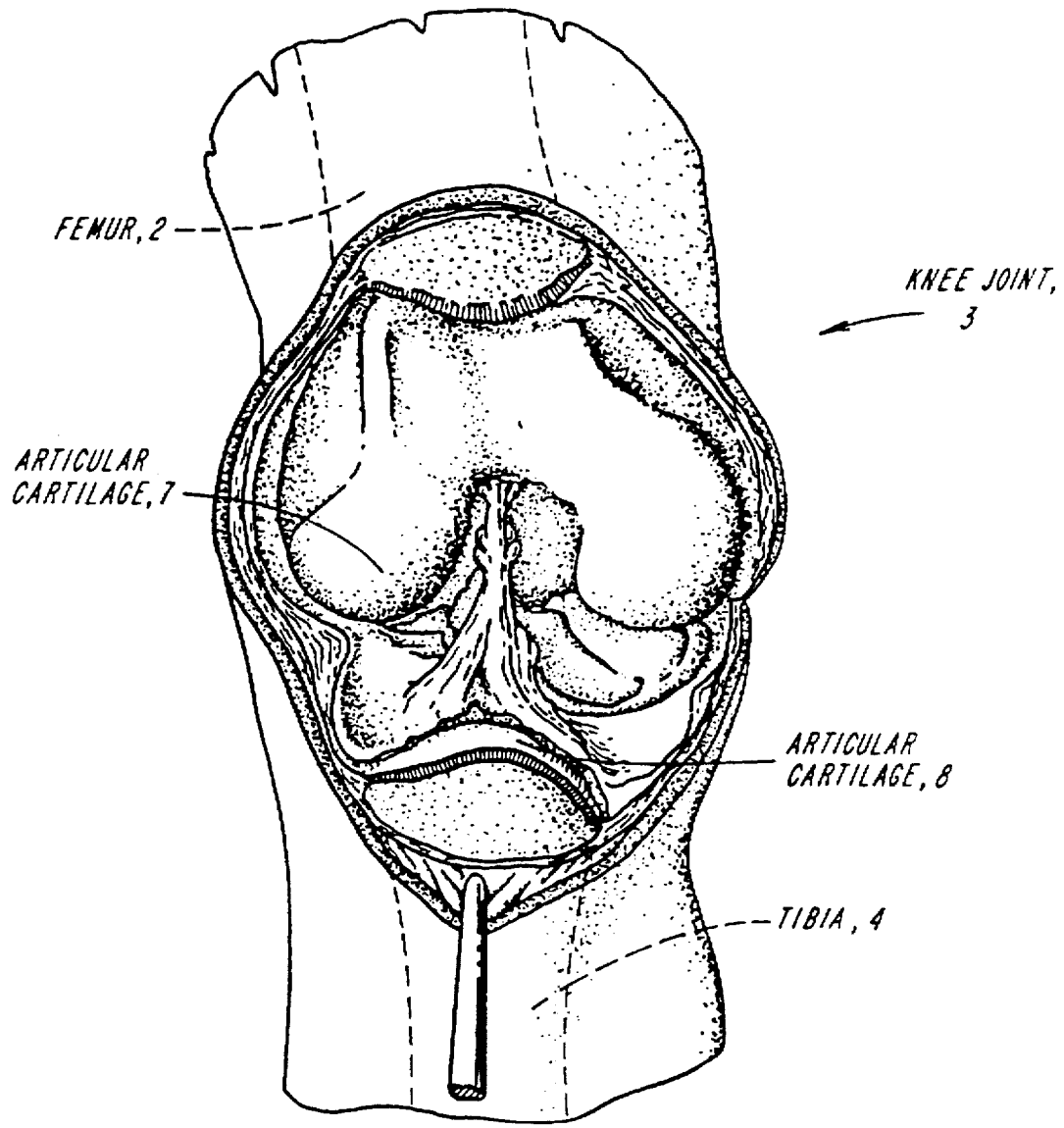
FIG. 1 shows a simplified diagrammatic representation of a human knee joint 3, showing the normal positioning of articular cartilage 7 on the articulating end of femur 2 and articular cartilage 8 on the articulating end of tibia 4.

The xenogeneic articular cartilage heterograft produced in accordance with the method of the invention is substantially non-immunogenic, while generally maintaining the mechanical properties of native articular cartilage. While the articular cartilage may undergo some shrinkage during processing, a xenogeneic articular cartilage heterograft prepared in accordance with the invention will have the general appearance of a native articular cartilage. The xenogeneic articular cartilage heterograft may also be cut into segments, each of which may be implanted into a joint of a recipient as set forth below.

The invention provides, in one embodiment, a method for preparing or processing a xenogeneic articular cartilage for engraftment into humans. As defined herein, "xenogeneic" means any non-human animal. Thus articular cartilage may be harvested from any non-human animal to prepare the heterografts of the invention. Articular cartilage from transgenic non-human animals or from genetically altered non-human animals may also be used as heterografts in accordance with the present invention. Preferably, bovine, ovine, or porcine knee joints serve as sources of the articular cartilage used to prepare the heterografts. More preferably, immature pig, calf or lamb knee joints are the sources of the articular cartilage, since the cartilage of younger animals may be inherently more elastic and engraftable than that of older animals. Most preferably, the age of the source animal is between six and eighteen months at time of slaughter.

In the first step of the method of the invention, an intact articular cartilage is removed from a joint of a non-human animal. Any joint may serve as the source of articular cartilage. Preferably articular cartilage from a corresponding donor joint is used to make the articular cartilage heterograft of the invention. For example, articular cartilage from a femero-tibial (stifle) joint is used to make an articular cartilage heterograft for implantation into a knee. Similarly, articular cartilage from a donor animal's hip joint is used to make an articular cartilage heterograft for a human hip joint. The joint which serves as the source of the articular cartilage should be collected from freshly killed animals and preferably immediately placed in a suitable sterile isotonic or other tissue preserving solution. Harvesting of the joints should occur as soon as possible after slaughter of the animal and should be performed in the cold, ie., in the approximate range 5°–20° C., to minimize enzymatic and/or bacterial degradation of the articular cartilage tissue. The articular cartilage is harvested from the joints in the cold, under strict sterile technique.

In accordance with the invention, a fine peel of articular cartilage with a small layer of subchondral bone is shaved from the donor joint to form the heterograft. The heterograft is then washed in about ten volumes of sterile cold water to remove residual blood proteins and water soluble materials. The heterograft is then immersed in alcohol at room temperature for about five minutes, to sterilize the tissue and to remove non-collagenous materials. In a preferred form of the invention, as heterograft appears a hyaline tissue supported on a bone substrate, having generally a spherical-shaped principal surface on the top side (the "superior surface"), with the under surface of bone (the "inferior surface") being rough.

After alcohol immersion, the heterograft may be directly implanted a prepared site at an articular surface of a human patient. Alternatively the heterograft may be subjected to at least one of the treatments set forth below. When more than one treatment is applied to the heterograft, the treatments may occur in any order. In one embodiment of the method of the invention, the heterograft may be treated by exposure to radiation, for example, by being placed in an ultraviolet radiation sterilizer such as the Stragene™ Model 2400, for about fifteen minutes. In another embodiment, the heterograft may be treated by again being placed in an alcohol solution. Any alcohol solution may be used to perform this treatment. Preferably, the heterograft is placed in a 70% solution of isopropanol at room temperature. In another embodiment, the heterograft may be subjected to ozonation.

In another embodiment, the heterograft may be treated by freeze/thaw cycling. For example, the heterograft may be frozen using any method of freezing, so long as the heterograft is completely frozen, ie., no interior warm spots remain which contain unfrozen tissue. Preferably, the heterograft is dipped into liquid nitrogen for about five minutes to perform this step of the method. More preferably, the heterograft is frozen slowly by placing it in a freezer. In the next step of the freeze/thaw cycling treatment, the heterograft is thawed by immersion in an isotonic saline bath at room temperature (about 25° C.) for about ten minutes. No external heat or radiation source is used, in order to minimize fiber degradation.

The heterograft may optionally be exposed to a chemical agent to tan or crosslink the proteins within the interstitial matrix, to further diminish or reduce the immunogenic determinants present in the heterograft. Any tanning or crosslinking agent may be used for this treatment, and more than one crosslinking step may be performed or more than one crosslinking agent may be used in order to ensure complete crosslinking and thus optimally reduce the immunogenicity of the heterograft. For example, aldehydes such as glutaraldehyde, formaldehyde, adipic dialdehyde, and the like, may be used to crosslink the collagen within the interstitial matrix of the heterograft in accordance with the method of the invention. Other suitable crosslinking agents include aliphatic and aromatic diamines, carbodiimides, diisocyanates, and the like. When glutaraldehyde is used as the crosslinking agent, for example, the heterograft may be placed in a buffered solution containing about 0.05 to about 5.0% glutaraldehyde and having a pH of about 7.4. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from three to five days. The crosslinking reaction should continue until the immunogenic determinants are substantially removed from the xenogeneic tissue, but the reaction should be terminated prior to significant alterations of the mechanical properties of the heterograft. When diamines are also used as crosslinking agents, the glutaraldehyde crosslinking should occur after the diamine crosslinking, so that any unreacted diamines are capped. After the crosslinking reactions have proceeded to completion as described above, the heterograft should be rinsed to remove residual chemicals, and 0.01–0.05 M glycine may be added to cap any unreacted aldehyde groups which remain.

Prior to treatment, the outer surface of the heterograft may optionally be pierced to increase permeability to agents used to render the heterograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the heterograft. Piercing may also be performed with a laser. In one form of the invention, one or more straight lines of punctures about three millimeters apart are established in the outer surface of the heterograft.

Prior to implantation, the articular cartilage heterograft of the invention may be treated with limited digestion by proteolytic enzymes such as ficin or trypsin to increase tissue flexibility, or with glycosidases to remove surface carbohydrate moieties, or coated with anticalcification agents, antithrombotic coatings, antibiotics, growth factors, or other drugs which may enhance the incorporation of the heterograft into the recipient knee joint. The articular cartilage heterograft of the invention may be further sterilized using known methods, for example, with additional glutaraldehyde or formaldehyde treatment, ethylene oxide sterilization, propylene oxide sterilization, or the like. The heterograft may be stored frozen until required for use.

The articular cartilage heterograft of the invention, or a segment thereof, may be implanted into damaged human joints by those of skill in the art using known arthroscopic surgical techniques. Specific instruments for performing arthroscopic techniques are known to those of skill in the art, which ensure accurate and reproducible placement of articular cartilage implants.

The underlying bone bed of the recipient joint is prepared with a bone burr to produce a cancellous bleeding bed. Grafting can involve either the entire articular surface or a portion of the articular surface. The substantially non-immunogenic articular cartilage heterograft of the invention is applied to the recipient joint as a cover, which is held in place by one or more suture anchors, absorbable pins, screws, staples, and the like. A fibrin clot may also be used to hold the substantially non-immunogenic articular cartilage heterograft in place.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of preparing an articular cartilage heterograft for implantation into a human, which comprises
   a. removing at least an intact portion of an articular cartilage from a joint of a nonhuman animal to provide a heterograft;
   b. washing the heterograft in water and alcohol; and
   c. digesting the heterograft with at least one glycosidase to remove surface carbohydrate moieties from the heterograft;

whereby the heterograft has substantially the same mechanical properties as the native articular cartilage.

2. The method according to claim 1, wherein said removing step includes removing with said portion a layer of subchondral bone.

3. The method according to claim 1, comprising the further step performed prior to step c of piercing the heterograft.

4. The method of claim 1, comprising the further step following step c of treating the heterograft with one or more agents selected from the group consisting of anticalcification agents, antithrombotic agents, antibiotics, and growth factors.

5. The method of claim 1, comprising the further step following step c of sterilizing the heterograft.

6. The method of claim 5, wherein said sterilizing step is selected from the group consisting of treatment with glutaraldehyde, treatment with formaldehyde, treatment with ethylene oxide, and treatment with propylene oxide.

* * * * *